United States Patent
Ren et al.

(10) Patent No.: US 11,365,293 B2
(45) Date of Patent: Jun. 21, 2022

(54) XYLAN-BASED DUAL NETWORK NANOCOMPOSITE HYDROGEL, PREPARATION METHOD THEREOF AND USE THEREFOR

(71) Applicant: SOUTH CHINA UNIVERSITY OF TECHNOLOGY, Guangzhou (CN)

(72) Inventors: Junli Ren, Guangzhou (CN); Weiqing Kong, Guangzhou (CN); Runcang Sun, Guangzhou (CN); Danyang Huang, Guangzhou (CN); Guibin Xu, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 676 days.

(21) Appl. No.: 16/317,838

(22) PCT Filed: Dec. 14, 2016

(86) PCT No.: PCT/CN2016/109906
§ 371 (c)(1),
(2) Date: Jan. 15, 2019

(87) PCT Pub. No.: WO2018/036025
PCT Pub. Date: Mar. 1, 2018

(65) Prior Publication Data
US 2021/0277188 A1    Sep. 9, 2021

(30) Foreign Application Priority Data
Aug. 22, 2016  (CN) .................. 201610701819.X

(51) Int. Cl.
*C08J 3/075*   (2006.01)
*A61L 27/20*   (2006.01)
(Continued)

(52) U.S. Cl.
CPC ............ *C08J 3/075* (2013.01); *A61L 27/20* (2013.01); *A61L 27/52* (2013.01); *A61L 2430/06* (2013.01);
(Continued)

(58) Field of Classification Search
CPC .... C08J 3/075; C08J 2305/00; C08J 2305/14; C08J 2351/02; A61L 27/20;
(Continued)

(56) References Cited

FOREIGN PATENT DOCUMENTS

| CN | 105461859 |   | 4/2016 |
|----|-----------|---|--------|
| CN | 105461859 A | * | 8/2021 |
| WO | 2012127119 |   | 9/2012 |

OTHER PUBLICATIONS

Chang et al., Xylan-Based Hydrogels as a Potential Carrier for Drug Delivery: Effect of Pore—Forming Agents, Pharmaceuticals, 10, 261. (Year: 2018).*

* cited by examiner

*Primary Examiner* — Carlos A Azpuru
(74) *Attorney, Agent, or Firm* — JMB Davis Ben-David

(57) ABSTRACT

This invention belongs to the technical field of composite materials, and discloses a xylan-based dual network nanocomposite hydrogel, preparation method thereof and use therefor. The method comprises (1) adding graphite oxide powder into deionized water, ultrasonically dispersing to obtain a GO aqueous dispersion; (2) adding xylan into deionized water, heating and stirring to obtain a xylan solution; (3) adding a water-soluble calcium salt, a reaction monomer and the xylan solution into the GO aqueous dispersion, and stirring and dispersing uniformly under an ice-bath condition, then adding an initiator, a crosslinking agent and an accelerator, stirring and mixing uniformly to obtain a mixed solution; and 4) drying and reacting the mixed solution (in the step (3) to obtain a xylan-based dual
(Continued)

network nanocomposite hydrogel. The composite hydrogel obtained by this invention has high mechanical property, is biodegradable and biocompatible, and can be used in the field of biomedicine, such as tissue engineering, drug sustained release, cell culture scaffold and cartilage tissue, etc.

7 Claims, 2 Drawing Sheets

(51) Int. Cl.
    *C08K 3/04*     (2006.01)
    *A61L 27/52*     (2006.01)
    *C08K 3/16*     (2006.01)
    *C08K 3/28*     (2006.01)

(52) U.S. Cl.
    CPC ........... *C08J 2305/00* (2013.01); *C08K 3/042* (2017.05); *C08K 2003/162* (2013.01); *C08K 2003/287* (2013.01)

(58) Field of Classification Search
    CPC ...... A61L 2430/06; A61L 27/44; A61L 27/58; A61K 47/36; A61K 47/32; C08K 3/04; C08K 2003/162; C08K 2003/287; C08K 3/16; C08F 2/44
    See application file for complete search history.

XYLAN-BASED DUAL NETWORK NANOCOMPOSITE HYDROGEL, PREPARATION METHOD THEREOF AND USE THEREFOR

CROSS-REFERENCE TO RELATED APPLICATIONS

This is the U.S. National Stage of International Patent Application No. PCT/CN2016/109906 filed Dec. 14, 2016, which was published in Chinese under PCT Article 21(2), and which in turn claims the benefit of China Patent Application No. 201610701819.X filed Aug. 22, 2016.

TECHNICAL FIELD

The invention belongs to the technical field of a composite material, and particularly relates to a xylan-based dual network nanocomposite hydrogel, preparation thereof and use therefor.

BACKGROUND

Hydrogel is a polymer network system that could absorb a large amount of water without dissolving and maintain a certain shape. Hydrogel has been widely used and studied in the fields such as drug sustained or controlled release, biomedicine and tissue engineering etc. However, some of the traditional chemically cross-linked hydrogel possess relatively weak mechanical properties, which greatly limit deeper and wider application of hydrogel. Especially in the aspects of biomedicine and tissue engineering, the requirement for the mechanical property of hydrogel is gradually emerging.

In recent years, a large amount of research has been devoted to improving the mechanical property of hydrogel. Polymer composite hydrogel and dual-network hydrogel have been always considered as common ways to effectively improve the mechanical property of gel. Polymer composite hydrogel, which is obtained by introducing reinforcing organic/inorganic fillers, such as montmorillonite, nanocellulose, carbon nanotubes, etc., into a polymer network structure of hydrogel, could improve the mechanical properties of the hydrogel. GO/PAM nanocomposite hydrogel has been reported (R. Liu, S. Liang, X.-Z. Tang, D. Yan, X. Li and Z. Z. Yu, J. Mater. Chem 2012, 22, 14160-14167; N. Zhang, R. Li, L. Zhang, H. Chen, W. Wang, Y. Liu, T. Wu, X. Wang, W. Wang and Y. Li, Soft Matter 2011, 7, 7231-7239; H. Wei, L. Han, Y. Tang, J. Ren, Z. Zhao and L. Jia, J. Mater. Chem. B 2015, 3, 1646-1654), but limited enhancement of mechanical strength is obtained, and compressive strength thereof is generally 1 MPa or less, which still has a lot of room for further improvement. The dual network hydrogel consists of two separate crosslinked networks, which improves the mechanical property of the hydrogel by introducing a new crosslinked network. However, most dual network hydrogels have the disadvantages such as serious environmental pollution, poor biocompatibility and poor degradability etc. Therefore, how to prepare a high-strength and biocompatible dual network composite hydrogel has become a challenge.

Xylan possesses good biocompatibility, renewability and special physical and chemical features. It could inhibit cell mutation, and is available for detoxification, anti-inflammatory, and anti-cancer effects, etc., which shows good prospects of application in medicine field. So far, no report has been found on such a dual network nanocomposite hydrogel, which has a grafted-polymerized network using xylan as a raw material, GO as a reinforcing filler, and acrylamide as a monomer, and another network formed by crosslinking graphene oxide (GO) and $Ca^{2+}$.

SUMMARY OF THE INVENTION

In order to overcome the shortcomings and deficiencies of the prior art, the primary object of the present invention is to provide a method for preparing a xylan-based dual network nanocomposite hydrogel.

Another object of the present invention is to provide a xylan-based dual network nanocomposite hydrogel prepared by the above method.

A further object of the present invention is to provide a use of the above xylan-based dual network nanocomposite hydrogel. The composite hydrogel could be applied in the field of biomedicine, in particular, tissue engineering, drug sustained release, cell culture scaffold, and cartilage tissue.

The objects of the present invention are achieved by the following technical solutions:

A method for preparing a xylan-based dual network nanocomposite hydrogel, comprises the following steps:

(1) adding graphite oxide powder (GO) into deionized water and ultrasonically dispersing to obtain a GO aqueous dispersion;

(2) adding xylan into deionized water, heating and stirring to obtain a xylan solution;

(3) adding a water-soluble calcium salt, a reaction monomer and the xylan solution into the GO aqueous dispersion, stirring and dispersing uniformly under an ice-bath condition, then adding an initiator, a cross-linking agent and an accelerator, stirring and mixing uniformly to obtain a mixed solution; the reaction monomer is one or more of acrylamide (AM), polyacrylamide, acrylic acid, N-isoacrylamide, and butyl acrylate, preferably acrylamide; and (4) drying and reacting the mixed solution in the step (3) to obtain a xylan-based dual network nanocomposite hydrogel.

The mass ratio of $Ca^{2+}$ in the water-soluble calcium salt in the step (3) to the GO in the GO aqueous dispersion is (10-240) mg: (20-60) mg, the mass ratio of the reaction monomer to the xylan is (1-6) g: (0.5-1.5) g, and the mass ratio of the GO in the GO aqueous dispersion to the xylan is (20-60) mg: (0.5-1.5) g.

The water-soluble calcium salt in the step (3) is $CaCl_2$ or calcium nitrate.

The drying and reacting in the step (4) is carried out at 50° C.-80° C. for 2 h-6 h.

The heating and stirring in the step (2) is stirring at 75° C.-95° C. for 0.5 h-1.5 h, and the concentration of the xylan solution is 0.05 g/mL-0.2 g/mL.

A temperature for the ultrasonically dispersing in the step (1) is at 20° C.-40° C., and a time for the dispersing is 2 h-6 h; and a power of the ultrasound is 100 W-300 W, and a frequency is 25 kHz-80 kHz.

The concentration of the GO aqueous dispersion in the step (1) is 0.4 mg/mL-6 mg/mL.

The initiator in the step (3) is ammonium persulfate or potassium persulfate; and the mass ratio of the initiator to the reaction monomer is (0.01-0.05) g: (1-6) g.

The crosslinking agent in the step (3) is N,N'-methylene bisacrylamide; and the mass ratio of the crosslinking agent to the reaction monomer is (0.0025-0.03) g: (1-6) g.

The accelerator in the step (3) is tetramethyl ethylene diamine or N,N,N',N'-tetramethylene ethylene diamine; and the volume-mass ratio of the accelerator to the reaction monomer is (10-50) μL: (1-6) g.

A xylan-based dual network nanocomposite hydrogel prepared by the above method is provided.

The xylan-based dual network nanocomposite hydrogel has a compressive strength of 0.17 MPa-2.3 MPa and an elongation of 629%-3967%.

A use of the xylan-based dual network nanocomposite hydrogel in the field of biomedicine is also provided, especially in tissue engineering, drug sustained release, cell culture scaffolds and cartilage tissue etc.

The preparation method and the obtained product of the invention have the following advantages and beneficial effects:

(1) The present invention combines the preparation methods for a nanocomposite hydrogel and a dual network hydrogel to prepare a high-strength hydrogel, which performs graft-copolymerization by using water as a solvent, xylan as a raw material, and a reaction monomer (acrylamide as the monomer) to form a layer of network, introduces GO as a reinforcing filler, and introduces $Ca^{2+}$ to cross-link with GO so as to form another layer of network. The method not only improves the mechanical strength of the hydrogel, but also improves the biocompatibility and biodegradability of the hydrogel;

(2) the preparation method of the invention uses a one-step synthesis method with simple operation, as well as mild and easily controlled reaction condition; and (3) the composite hydrogel obtained by the invention has higher mechanical properties, meanwhile, is biodegradable, has good biocompatibility, and can be applied in biomedical fields, such as tissue engineering, drug sustained release, cell culture scaffold and cartilage tissue etc.

DETAILED DESCRIPTION OF THE EMBODIMENTS

Figure 1:
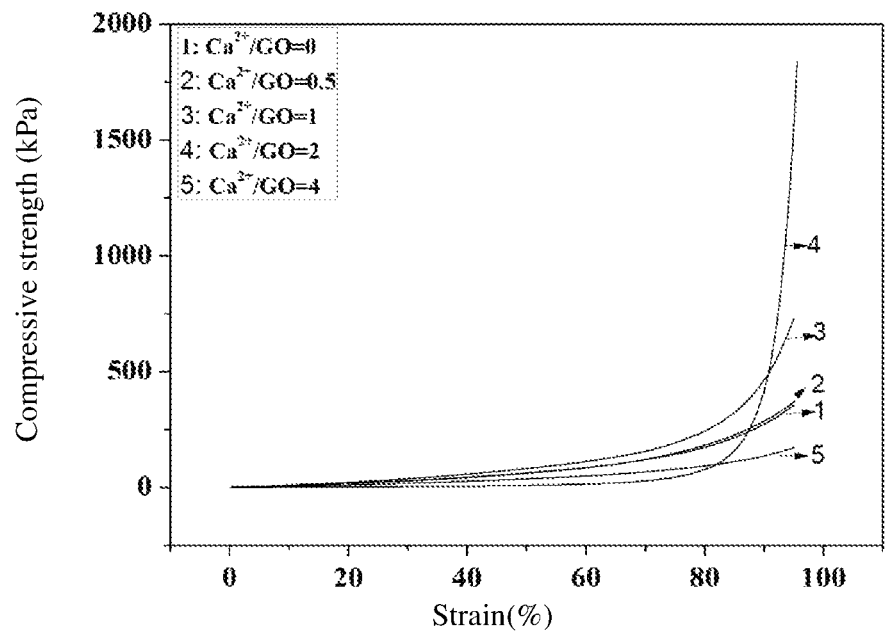
FIG. 1 shows compression stress-strain curves of hydrogels with different $Ca^{2+}$ contents (Comparative Example 1 (1: $Ca^{2+}/GO=0$), Example (2: $Ca^{2+}/GO=0.5$), Example 2 (4: $Ca^{2+}/GO=2$), Example 6 (3: $Ca^{2+}/GO=1$) and Example 7 (5: $Ca^{2+}/GO=4$))

The present invention will be further described in detail below with reference to examples and the drawings, but the embodiments of the present invention are not limited thereto.

Comparative Example 1

A method for preparing a GO/PAM/XH hydrogel material comprises the following steps:

(1) adding 20 mg of graphite oxide powder (GO) into 10 mL of deionized water, and ultrasonically dispersing (100 W, 25 kHz) at 20° C. for 4 h to obtain a GO aqueous dispersion;

(2) weighing 1 g of xylan, dissolving the same in 10 mL of deionized water, and stirring at 85° C. for 1 h to form a uniform xylan solution;

(3) adding 4 g of a monomer acrylamide (AM) and the xylan solution into the GO aqueous dispersion in the step (1), stirring and dispersing uniformly under an ice-bath condition; adding 0.01 g of an initiator ammonium persulfate, 0.008 g of a cross-linking agent N,N'-methylene bisacrylamide and 40 µL of an accelerator tetramethyl ethylene diamine, and stirring uniformly to obtain a mixed solution; and (4) placing the mixed solution in the step (3) in an oven to react at 50° C. for 2 hours to obtain a composite hydrogel, that is, a GO/PAM/XH hydrogel material. The performance-testing curves of the composite hydrogel are shown as FIG. 1 and FIG. 2.

The GO/PAM/XH composite hydrogel obtained in this Comparative Example had a maximum compressive strength of 0.17 MPa and an elongation of 629% when the compressive deformation reached 95%.

Example 1

A method for preparing a xylan-based dual network nanocomposite hydrogel ($GO/Ca^{2+}/PAM/XH$ hydrogel) material, comprises the following steps:

(1) adding 20 mg of graphite oxide powder (GO) into 10 mL of deionized water, and ultrasonically dispersing (100 W, 40 kHz) at 20° C. for 4 h to obtain a GO aqueous dispersion;

(2) weighing 1 g of xylan, dissolving the same in 10 mL of deionized water, and stirring at 85° C. for 1 h to form a uniform xylan solution;

(3) adding 27.75 mg of $CaCl_2$, 4 g of a monomer acrylamide and the xylan solution into the GO aqueous dispersion in the step (1), stirring and dispersing uniformly under an ice-bath condition; adding 0.01 g of an initiator ammonium persulfate, 0.01 g of a crosslinking agent N,N'-methylene bisacrylamide and 50 µL of an accelerator tetramethyl ethylene diamine, and stirring uniformly to obtain a mixed solution; and (4) placing the mixed solution in the step (3) in an oven to react at 60° C. for 4 h to obtain a xylan-based dual network nanocomposite hydrogel ($GO/Ca^{2+}/PAM/XH$ composite hydrogel). The performance-testing curves of the composite hydrogel are shown as FIG. 1 and FIG. 2.

The $GO/Ca^{2+}/PAM/XH$ composite hydrogel obtained in this example was not broken and crushed when the compressive deformation reached 95%, and could recover rapidly after compression. The compressive strength of the hydrogel was 0.184 MPa, and the elongation thereof was 775%.

Example 2

A method for preparing a xylan-based dual network nanocomposite hydrogel ($GO/Ca^{2+}/PAM/XH$ composite hydrogel) comprises the following steps:

(1) adding 20 mg of graphite oxide powder (GO) into 10 mL of deionized water, and ultrasonically dispersing (200 W, 40 kHz) at 30° C. for 4 h to obtain a GO aqueous dispersion;

(2) weighing 1 g of xylan, dissolving the same in 10 mL of deionized water, and stirring at 85° C. for 1 h to form a uniform xylan solution;

(3) adding 111 mg of $CaCl_2$, 4 g of a monomer acrylamide and the xylan solution into the GO aqueous dispersion in the step (1), stirring and dispersing uniformly under an ice-bath condition; adding 0.03 g of an initiator ammonium persulfate, 0.01 g of an crosslinking agent N,N'-methylene bisacrylamide and 50 µL of an accelerator tetramethyl ethylene diamine, and stirring uniformly to obtain a mixed solution; and (4) placing the mixed solution in the step (3) in an oven to react at 60° C. for 4 h to obtain a xylan-based dual network nanocomposite hydrogel (GO/Ca$^{2+}$/PAM/XH composite hydrogel). The performance-testing curves of the composite hydrogel are shown as FIGS. 1, 2 and 3.

The GO/Ca$^{2+}$/PAM/XH composite hydrogel obtained in this example was not broken and crushed when the compressive deformation reached 95%, and could recover rapidly after compression. The compressive strength of the hydrogel was 1.84 MPa, and the elongation thereof was 1918%.

Example 3

A method for preparing a xylan-based nanocomposite hydrogel (GO/Ca$^{2+}$/PAM/XH composite hydrogel) material of this Example comprises the following steps:
(1) adding 4 mg of graphite oxide powder (GO) into 10 mL of deionized water, and ultrasonically dispersing (200 W, 40 kHz) at 30° C. for 2 h to obtain a GO aqueous dispersion;
(2) weighing 1 g of xylan, dissolving the same in 10 mL of deionized water, and stirring at 85° C. for 1 h to form a uniform xylan solution;
(3) adding 22.2 mg of CaCl$_2$, 4 g of a monomer acrylamide and the xylan solution into the GO aqueous dispersion in the step (1), stirring and dispersing uniformly under an ice-bath condition; adding 0.03 g of an initiator ammonium persulfate, 0.01 g of an crosslinking agent N,N'-methylene bisacrylamide and 20 μL of an accelerator tetramethyl ethylene diamine, and stirring uniformly to obtain a mixed solution; and
(4) placing the mixed solution in the step (3) in an oven to react at 60° C. for 4 h to obtain a xylan-based dual network nanocomposite hydrogel (GO/Ca$^{2+}$/PAM/XH composite hydrogel).

The GO/Ca$^{2+}$/PAM/XH composite hydrogel obtained in this example was not broken and crushed when the compressive deformation reached 95%, and could recover rapidly after compression. The compressive strength of the hydrogel was 1.1 MPa, and the elongation thereof was 1100%.

Example 4

A method for preparing a carboxymethyl xylan-based nanocomposite hydrogel (GO/Ca$^{2+}$/PAM/XH hydrogel) material of this Example comprises the following steps:
(1) adding 60 mg of graphite oxide powder (GO) into 10 mL of deionized water, and ultrasonically dispersing (300 W, 80 kHz) at 40° C. for 6 h to obtain a GO aqueous dispersion;
(2) weighing 1 g of xylan, dissolving the same in 10 mL of deionized water, and stirring at 85° C. for 1 h to form a uniform xylan solution;
(3) adding 166.5 mg of CaCl$_2$, 4 g of a monomer acrylamide and the xylan solution into the GO aqueous dispersion in the step (1), stirring and dispersing uniformly under an ice-bath condition; adding 0.05 g of an initiator ammonium persulfate, 0.01 g of an crosslinking agent N,N'-methylene bisacrylamide and 50 μL of an accelerator tetramethyl ethylene diamine, and stirring uniformly to obtain a mixed solution; and
(4) placing the mixed solution in the step (3) in an oven to react at 80° C. for 6 h to obtain a xylan-based dual network nanocomposite hydrogel (GO/Ca$^{2+}$/PAM/XH composite hydrogel).

The GO/Ca$^{2+}$/PAM/XH composite hydrogel obtained in this example was not broken and crushed when the compressive deformation reached 95%, and could recover rapidly after compression. The compressive strength of the hydrogel was 2.3 MPa, and the elongation thereof was 3310%.

Example 5

A method for preparing a xylan-based nanocomposite hydrogel (GO/Ca$^{2+}$/PAM/XH composite hydrogel) material comprises the following steps:
(1) adding 60 mg of graphite oxide powder (GO) into 10 mL of deionized water, and ultrasonically dispersing (300 W, 80 kHz) at 30° C. for 6 h to obtain a GO aqueous dispersion;
(2) weighing 1 g of xylan, dissolving the same in 10 mL of deionized water, and stirring at 85° C. for 1 h to form a uniform xylan solution;
(3) adding 166.5 mg of CaCl$_2$, 4 g of a monomer acrylamide and the xylan solution into the GO aqueous dispersion in the step (1), stirring and dispersing uniformly under an ice-bath condition; adding 0.05 g of an initiator ammonium persulfate, 0.005 g of an crosslinking agent N,N'-methylene bisacrylamide and 50 μL of an accelerator tetramethyl ethylene diamine, and stirring uniformly to obtain a mixed solution; and
(4) placing the mixed solution in the step (3) in an oven to react at 80° C. for 6 h to obtain a xylan-based dual network nanocomposite hydrogel (GO/Ca$^{2+}$/PAM/XH composite hydrogel).

The GO/Ca$^{2+}$/PAM/XH composite hydrogel obtained in this example was not broken and crushed when the compressive deformation reached 95%, and could recover rapidly after compression. The compressive strength of the hydrogel was 1.63 MPa, and the elongation thereof was 3976%.

Example 6

A method for preparing a xylan-based dual network nanocomposite hydrogel (GO/Ca$^{2+}$/PAM/XH composite hydrogel) comprises the following steps:
(1) adding 20 mg of graphite oxide powder (GO) into 10 mL of deionized water, and ultrasonically dispersing (200 W, 40 kHz) at 30° C. for 4 h to obtain a GO aqueous dispersion;
(2) weighing 1 g of xylan, dissolving the same in 10 mL of deionized water, and stirring at 85° C. for 1 h to form a uniform xylan solution;
(3) adding 55.5 mg of CaCl$_2$, 4 g of a monomer acrylamide and the xylan solution into the GO aqueous dispersion in the step (1), stirring and dispersing uniformly under an ice-bath condition; adding 0.03 g of an initiator ammonium persulfate, 0.01 g of an crosslinking agent N,N'-methylene bisacrylamide and 50 μL of an accelerator tetramethyl ethylene diamine, and stirring uniformly to obtain a mixed solution; and
(4) placing the mixed solution in the step (3) in an oven to react at 60° C. for 4 h to obtain a xylan-based dual network nanocomposite hydrogel (GO/Ca$^{2+}$/PAM/XH composite hydrogel). The performance-testing curves of the composite hydrogel are shown as FIGS. 1 and 2.

The GO/Ca$^{2+}$/PAM/XH composite hydrogel obtained in this example was not broken and crushed when the compressive deformation reached 95%, and could recover rapidly after compression. The compressive strength of the hydrogel was 0.757 MPa, and the elongation thereof was 942%.

Example 7

A method for preparing a xylan-based dual network nanocomposite hydrogel (GO/Ca$^{2+}$/PAM/XH composite hydrogel) material comprises the following steps:

(1) adding 20 mg of graphite oxide powder (GO) into 10 mL of deionized water, and ultrasonically dispersing (200 W, 40 kHz) at 30° C. for 4 h to obtain a GO aqueous dispersion;

(2) weighing 1 g of xylan, dissolving the same in 10 mL of deionized water, and stirring at 85° C. for 1 h to form a uniform xylan solution;

(3) adding 222 mg of CaCl$_2$, 4 g of a monomer acrylamide and the xylan solution into the GO aqueous dispersion in the step (1), stirring and dispersing uniformly under an ice-bath condition; adding 0.03 g of an initiator ammonium persulfate, 0.01 g of an crosslinking agent N,N'-methylene bisacrylamide and 50 µL of an accelerator tetramethyl ethylene diamine, and stirring uniformly to obtain a mixed solution; and (4) placing the mixed solution in the step (3) in an oven to react at 60° C. for 4 h to obtain a xylan-based dual network nanocomposite hydrogel (GO/Ca$^{2+}$/PAM/XH composite hydrogel). The performance-testing curves of the composite hydrogel are shown as FIG. 1 and FIG. 2.

The GO/Ca$^{2+}$/PAM/XH composite hydrogel obtained in this example was not broken and crushed when the compressive deformation reached 95%, and could recover rapidly after compression. The compressive strength of the hydrogel was 0.175 MPa, and the elongation thereof was 630%.

Figure 2:
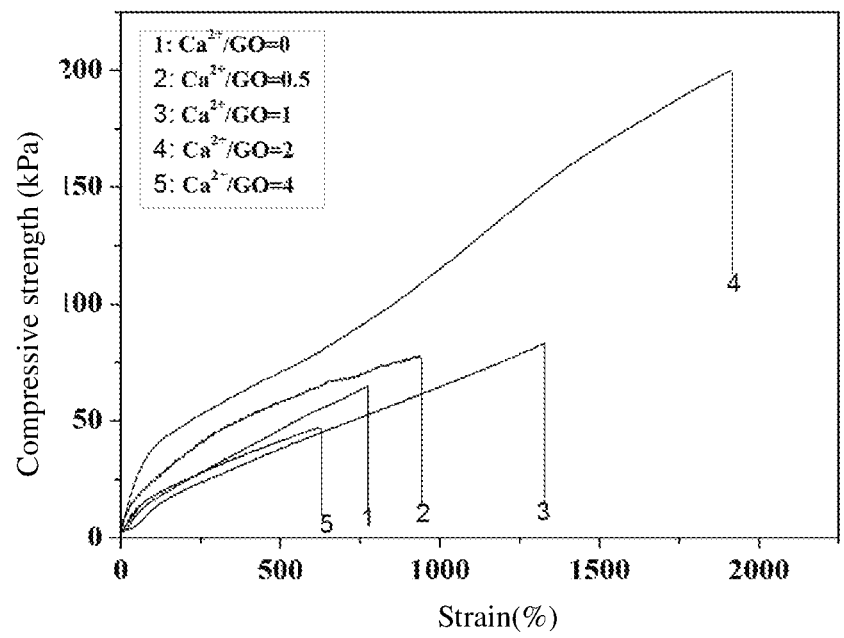
FIG. 2 shows tensile stress-strain curves of hydrogels with different $Ca^{2+}$ content (Comparative Example 1 (1: $Ca^{2+}/GO=0$), Example 1 (2: $Ca^{2+}/GO=0.5$), Example 2 (4: $Ca^{2+}/GO=2$), Example 6 (3: $Ca^{2+}/GO=1$) and Example 7 (5: $Ca^{2+}/GO=4$))

FIGS. 1 and 2 show compressive stress-strain curves and tensile stress-strain curves of hydrogels with different ratios of Ca$^{2+}$/GO (Comparative Example 1, Examples 1, 2, 6, and 7), respectively. It can be seen that the content of Ca$^{2+}$ has a great influence on the mechanical strength of the GO/PAM/XH composite hydrogel. When 20 mg of GO and 0.01 g of the crosslinking agent are used without Ca$^{2+}$, the maximum compressive strength is 0.17 MPa and the maximum elongation is 629% while compressive deformation reaches 95%. However, after a small amount of Ca$^{2+}$ (Ca$^{2+}$/GO=0.5-2) is introduced into the GO/PAM/XH hydrogel network to form a second network, the mechanical strength of the hydrogel is significantly improved. When the ratio of Ca$^{2+}$/GO is increased from 0.5 to 2, and when the compressive deformation reaches 95%, the hydrogel is not broken and crushed, the compressive strength of the hydrogel increases from 0.184 MPa to 1.84 MPa, and the elongation increases from 775% to 1918%. That is, when the amount of Ca$^{2+}$ is twice that of GO, the compressive strength is increased to 10 times the original compresseive strength, and the elongation is increased to nearly 3 times the original elongation. This is because Ca$^{2+}$ could cross-link with GO to form another layer of network structure, while the XH and AM graft-copolymerized cross-linking network and the Ca$^{2+}$ and GO cross-linking network could be connected by covalent bonds, so that GO/Ca$^{2+}$/PAM/XH hydrogel exhibits excellent mechanical property as well as very high elasticity and toughness. However, when the amount of Ca$^{2+}$ continues to increase (Ca$^{2+}$/GO=3-4), the compressive strength and the elongation of the hydrogel both decrease gradually. When the ratio of Ca$^{2+}$/GO is increased from 2 to 4, and when the compression deformation reaches 95%, the compressive strength of the hydrogel decreases from 1.84 MPa to 0.37 MPa and the elongation decreases from 1918% to 942%. This is because GO acts as new chemical cross-linking points on one hand, and combines with Ca$^{2+}$ to form another network on the other hand. With a further increase of the content of Ca$^{2+}$, the chemical crosslinking points relatively decrease, resulting in certain decline of the mechanical property. It can be seen from the above, that the introduction of the network of Ca$^{2+}$ and GO can effectively improve the mechanical strength of the hydrogel, and when the ratio of Ca$^{2+}$/GO is 2, the highest mechanical strength is obtained.

Figure 3:
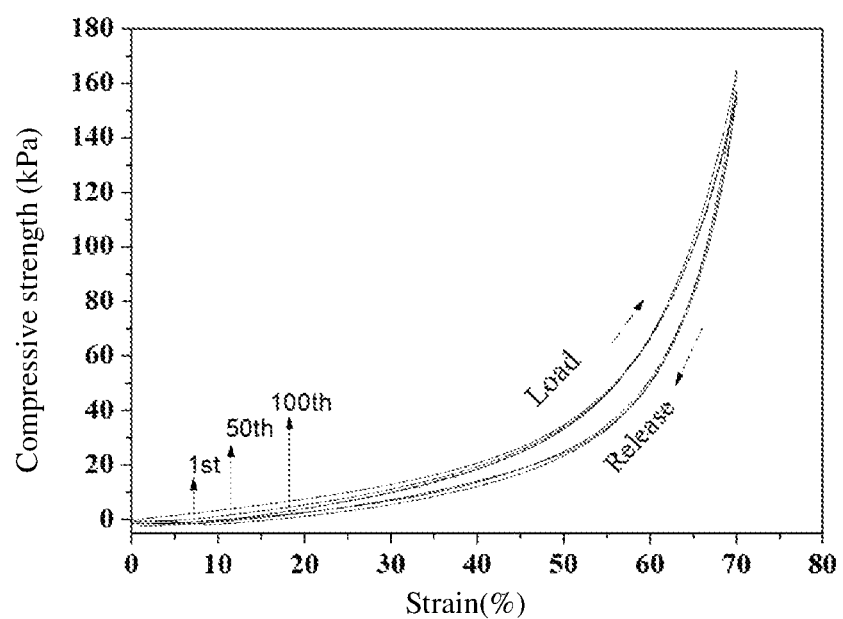
FIG. 3 is a cyclic compression stress-strain curve of the $GO/Ca^{2+}/PAM/XH$ composite hydrogel in Example 2.

FIG. 3 is a cyclic compressive stress-strain curve of the GO/Ca$^{2+}$/PAM/XH composite hydrogel of Example 2. When the ratio of Ca$^{2+}$/GO is 2, the amount of GO is 20 mg, the amount of the cross-linking agent is 0.01 g. Furthermore, when the compressive deformation reaches 70%, the hydrogel is not broken and crushed, and maintains good elasticity. After releasing pressure, the hydrogel can rapidly recover to its original shape. Moreover, after 100 cycles of compressing-releasing, the hydrogel has almost no plastic deformation and decrease in compressive strength. Such high-strength hydrogel is expected to be used in biomedical fields such as tissue engineering, drug sustained release, cell culture scaffolds, and cartilage tissue, etc.

The above examples are preferred embodiments of the present invention, but the embodiments of the present invention are not limited to the above examples, and any other changes, modifications, substitutions, combinations, and simplifications made without departing from the spirit and principle of the present invention should all be equivalent replacement modes and be included in the protection scope of the present invention.

The invention claimed is:

1. A method for preparing a xylan-based dual network nanocomposite hydrogel, comprising the following steps:
   (1) adding graphite oxide powder into deionized water and ultrasonically dispersing to obtain a graphite oxide aqueous dispersion;
   (2) adding xylan to deionized water, heating and stirring to obtain a xylan solution;
   (3) adding a water-soluble calcium salt, a reaction monomer and the xylan solution into the graphite oxide aqueous dispersion, stirring and dispersing uniformly under an ice-bath condition, then adding an initiator, a cross-linking agent and an accelerator, stirring and mixing uniformly to obtain a mixed solution, the reaction monomer is one or more of acrylamide, polyacrylamide, acrylic acid, N-isoacrylamide, and butyl acrylate; and
   (4) drying and reacting the mixed solution in the step (3) to obtain a xylan-based dual network nanocomposite hydrogel.

2. The method for preparing the xylan-based dual network nanocomposite hydrogel according to claim 1, wherein the mass ratio of Ca$^{2+}$-in the water-soluble calcium salt in the step (3) to the graphite oxide powder in the graphite oxide aqueous dispersion is (10-240) mg: (20-60) mg, the mass ratio of the reaction monomer to the xylan is (1-6) g: (0.5-1.5) g, and the mass ratio of the graphite oxide powder in the graphite oxide aqueous dispersion to the xylan is (20-60) mg: (0.5-1.5) g.

3. The method for preparing the xylan-based dual network nanocomposite hydrogel according to claim 1, wherein the water-soluble calcium salt in the step (3) is CaCl$_2$) or calcium nitrate; the initiator is ammonium persulfate or potassium persulfate; the crosslinking agent is N,N' methylene bisacrylamide; and the accelerator is tetramethyl ethylene diamine or N,N,N',N'-tetramethylene ethylene diamine.

4. The method for preparing the xylan-based dual network nanocomposite hydrogel according to claim 1, wherein the drying and reacting in the step (4) is carried out at 50° C.-80° C. for 2 h-6 h; and the heating and stirring in the step (2) is stirring at 75° C.-95° C. for 0.5 h-1.5 h.

5. The method for preparing the xylan-based dual network nanocomposite hydrogel according to claim 1, wherein the concentration of the graphite oxide aqueous dispersion in the step (1) is 0.4 mg/mL-6 mg/mL, and the concentration of the xylan solution in the step (2) is 0.05 g/mL-0.2 g/mL.

6. The method for preparing the xylan-based dual network nanocomposite hydrogel according to claim 1, wherein the mass ratio of the initiator to the reaction monomer in the step (3) is (0.01-0.05) g: (1-6) g; the mass ratio of the crosslinking agent to the reaction monomer in the step (3) is (0.0025-0.03) g: (1-6) g; and the volume-mass ratio of the accelerator to the reaction monomer in the step (3) is (10-50) μL: (1-6) g.

7. The method for preparing a xylan-based dual network nanocomposite hydrogel according to claim 1, wherein the ultrasonically dispersing in the step (1) is carried out at 20° C.-40° C. for 2 h-6 h; and the power of the ultrasound is 100 W-300 W, and the frequency is 25 kHz-80 kHz.

* * * * *